US009909127B2

United States Patent
Zhang et al.

(10) Patent No.: US 9,909,127 B2
(45) Date of Patent: *Mar. 6, 2018

(54) INHIBITOR FOR INHIBITING AVIAN INFLUENZA VIRUS AND A PHARMACEUTICAL COMPOSITION CONTAINING THE SAME

(71) Applicant: JIANGSU MICROMEDMARK BIOTECH CO., LTD., Jiangsu (CN)

(72) Inventors: Chenyu Zhang, Beijing (CN); Ke Zeng, Beijing (CN); Jin Wang, Beijing (CN); Xihan Li, Beijing (CN); Hongwei Gu, Beijing (CN)

(73) Assignee: JIANGSU MICROMEDMARK BIOTECH CO., LTD., Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/103,021

(22) PCT Filed: Dec. 9, 2014

(86) PCT No.: PCT/CN2014/093383
§ 371 (c)(1),
(2) Date: Jun. 9, 2016

(87) PCT Pub. No.: WO2015/085903
PCT Pub. Date: Jun. 18, 2015

(65) Prior Publication Data
US 2016/0312221 A1 Oct. 27, 2016

(30) Foreign Application Priority Data
Dec. 9, 2013 (CN) .......................... 2013 1 0666658

(51) Int. Cl.
| | | |
|---|---|---|
| *C12N 15/11* | (2006.01) | |
| *C12N 15/113* | (2010.01) | |
| *C12Q 1/68* | (2018.01) | |
| *C12Q 1/70* | (2006.01) | |
| *A61K 31/713* | (2006.01) | |
| *A61K 31/7105* | (2006.01) | |

(52) U.S. Cl.
CPC .......... *C12N 15/113* (2013.01); *A61K 31/713* (2013.01); *A61K 31/7105* (2013.01); *C12N 15/1131* (2013.01); *C12Q 1/689* (2013.01); *C12Q 1/701* (2013.01); *C12N 15/11* (2013.01); *C12N 2310/113* (2013.01); *C12N 2310/141* (2013.01); *C12N 2320/30* (2013.01); *C12Q 2600/178* (2013.01)

(58) Field of Classification Search
CPC ................ C12N 15/113; C12N 2310/141
See application file for complete search history.

(56) References Cited

U.S. PATENT DOCUMENTS

2011/0118332 A1* 5/2011 Cullen ............... C12N 15/1133
514/44 A
2012/0070865 A1 3/2012 Rybak et al.

FOREIGN PATENT DOCUMENTS

CN 101670117 A 3/2010

OTHER PUBLICATIONS

Influenza A virus (A/Hong Kong/156/97(H5N1)) partial HA gene for hemagglutinin, genomic RNA, GenBank AM922150.1, data date: Jul. 26, 2016, accessed and retrieved from ncbi.nlm.nih.gov on Dec. 29, 2016.*
Hemagglutinin, partial [Influenza A virus (A/Hong Kong/156/97(H5N1))], GenBank CAP58163.1, data date: Jul. 26, 2016, accessed and retrieved from ncbi.nlm.nih.gov on Dec. 29, 2016.*
Influenza A virus (A/turkey/Turkey/Manyas 257/2005(H5N1)) hemagglutinin (HA) gene, partial cds, GenBank EU542732.1, data date: Jul. 26, 2016, accessed and retrieved from ncbi.nlm.nih.gov on Dec. 29, 2016.*
Seo et al., Evolutionarily conserved function of a viral microRNA, 2008, Journal of Virology, vol. 82, pp. 9823-9828.*
Otaegi et al., An optimized sponge for microRNA miR-9 affects spinal motor neuron development in vivo, 2012, Frontiers in Neuroscience, vol. 5, pp. 1-9.*
International Search Report dated Mar. 25, 2015, issued in corresponding PCT/CN2014/093383, 4 pages.
English translation Abstract of CN101670117 published Mar. 17, 2010 (1 page).
Cao, Xuesong et al., "Analysis of Regulation Role of sRNA (istR) in *Salmonella* Resistant to Reactive Nitrogen and Oxygen Intermediates", Microbiology China, Aug. 20, 2011, pp. 1241-1248, abstract (1 page).
Meng, Xia et al., "Research on the Regulation Functions of Pathopoiesis of Small Non-coding RNA of Pathogens", Chinese Journal of Preventive Veterinary Medicine, vol. 33, No. 9, Dec. 31, 2011, pp. 1803-1808, abstract (1 page).
Shi, Chunmei et al. "Construction and Validation of Silencing Vector Hsa-miR-26b", Chinese Journal of Clinical Laboratory Science, vol. 31, No. 7, Jul. 31, 2013, pp. 503-506, abstract (1 page).
Vogel, Jorg et al., "Small Non-coding RNAs and the Bacterial Outer Membrane", Current Opinion in Microbiology, vol. 9, Dec. 31, 2006, pp. 605-611.

\* cited by examiner

*Primary Examiner* — Dana H Shin
(74) *Attorney, Agent, or Firm* — Millen, White, Zelano & Branigan, P.C.

(57) ABSTRACT

Provided is non-coded RNA of in-vivo infected microorganisms, parasitic microorganisms, symbiotic microorganisms and identification and application thereof. Also provided is a method of identifying the non-coded RNA of in-vivo pathogen sources. The invention also provided a pharmaceutical composition containing an inhibitor for specifically inhibiting or blocking a RNA sequence and a method to treat a pathogen infectious disease or parasitic disease by administering an inhibitor, which inhibits a non-coding RNA sequence derived from a pathogen in the body of an animal, to an animal subject in need thereof.

3 Claims, 7 Drawing Sheets

INHIBITOR FOR INHIBITING AVIAN INFLUENZA VIRUS AND A PHARMACEUTICAL COMPOSITION CONTAINING THE SAME

TECHNICAL FIELD

The present invention pertains to the field of biotechnology, more particularly to non-coding RNAs of in vivo infectious microorganisms, parasitic microorganisms and symbiotic microorganisms and identification and application thereof.

BACKGROUND ART

Microorganism is a general term for tiny organisms which are widely distributed in nature and not visible to the naked eye, but can only be observed being magnified under an optical microscope or an electron microscope by hundreds, thousands or even tens of thousands of times. They have characteristics such as a tiny size, a simple structure, rapid reproduction, easy variation and strong adaptive capacity to environment.

The microorganisms are of wide varieties, and are extremely widely distributed in nature. Human, animals and plants carry a variety of microorganisms are also present on body surfaces and cavities communicating with the exterior.

One of the most important influences of microorganisms on human is to cause some diseases, especially infectious diseases. Although great progresses have been made in the prevention and treatment of diseases, newly occurring and recurring microbial infections continue to appear, and effective therapeutic drugs against many diseases are lacking all the time. Furthermore, the strong selection pressure caused by the overuse of a large number of broad-spectrum antibiotics lead many strains to mutate, resulting in the appearence of more dangerous drug-resistant strains.

All microorganisms growing in a living body in vitro or in vivo are called parasitic microorganisms, and the microorganisms in parasitic life-style make a living by depriving nutrition of other organisms, even depending on some parts of the bodies of other organisms as nutrients. Microorganisms can enter a human or animal body through the mouth, skin or respiratory tract, and grow and reproduce making use of the nutrition of the human or animal body. If these bacteria produce toxins, humans will be met with illnesses such as cholera, typhoid and pneumonia. Diseases such as AIDS and common cold are caused by viruses. Viruses are more specific parasitic microorganisms; because they cannot live away from living cells, they are called as strictly parasitic microorganisms.

Microbial infections are common clinical diseases caused by microorganisms. For the diagnosis of most of bacterial diseases, bacteriological diagnosis is required in order to determine the causes of diseases. However, some bacteria being isolated from a specimen does not necessarily mean that this bacterial species is the pathogen of the disease, and thus a comprehensive analysis shall be performed according to the clinical situation of the patient, the specimen collection site, and the species of the isolated bacteria. Sometimes virulence, cell and animal tests shall be made to determine pathogenicity of the strain.

Since bacteria and their metabolites have antigenicity, bacterial infections can also be diagnosed by detecting antibodies. Furthermore, gene diagnosis, a new method for diagnosing bacteria by detecting genetic materials of bacteria, is developed in recent years. However, the detection method mentioned above requires tedious operation, strict conditions in the collection and preservation of samples, and a long detection period, which could easily lead to delays of the patient's condition, but produces a high false positive rate in the test results.

Laboratory tests for virus infection include viral isolation and identification, direct detection of viral nucleic acids and antigens, and detection of specific antibodies. A defect of the existing viral detection methods is in that the requirements on the collection, storage and transportation of samples required for the virus detection are more stringent, and the sample collection is easily affected by subjective factors of the collector, resulting in high false positive or negative rate of the virus detection that can affect the clinical outcomes.

An infectious disease, especially a chronic persistent infection, is one of global stubborn diseases harmful to the human health and life. Intracellular pathogens forming a significant impact on human include *Mycobacterium tuberculosis, Salmonella, Brucella, Legionella pneumophila, Listeria*, and *Mycobacterium leprea*. Seven diseases, including tuberculosis, AIDS and hepatitis, form global threats, and are difficult to treat for the reason closely relating to the intracellular parasitism of pathogens.

It is a tough problem to treat intracellular microbial infections. The main reason includes: when the pathogens invade and lie dormant in the cells, it is difficult to deliver a conventional antibiotic to the cells where the pathogens hide, and even if delivered, it is difficult to achieve an effective microbicidal effect at the concentration of antibiotic; antibodies could hardly enter the cells to play a role; and when the intracellular bacteria are successfully living in cells, they could not only escape from the immune phagocytosis, killing and clearance, but also exist for a long time in the cells and lead to physical diseases when the time is convenient (e.g., when immunity of the body decreases).

Therefore, new diagnostic and therapeutic techniques are in urgent need for microbial infectious diseases with simple operation and accurate results so as to improve the laboratory diagnosis and clinical treatment of such diseases, and to avoid delays of the patient's condition and reduce the physical and economic burden of patient.

SUMMARY OF INVENTION

An object of the present invention is to provide a diagnostic and therapeutic method for microbial infections with simple operation and accurate results.

In the first aspect of the present invention, provided are isolated non-coding RNA (ncRNA) sequences that are non-coding RNA (ncRNA) sequences released by in vivo pathogens of animals.

In another preferred example, the non-coding RNA sequences are specific to the in vivo pathogens, and do not exist in body of a healthy animal.

In another preferred example, the healthy animal refers to an animal not infected or parasitized by the pathogens.

In another preferred example, the pathogens include infectious microorganisms, parasitic microorganisms and/or symbiotic microorganisms.

In another preferred example, the pathogens include bacteria, archaea, viruses, chlamydiae, mycoplasmas and protists.

In another preferred example, the pathogens include *Salmonella*, influenza virus, parainfluenza virus, *Neisseria*, avian influenza virus, hepatitis virus, respiratory syncytial virus, Coxsackie virus and herpes virus.

In another preferred example, the non-coding RNAs include microRNA, siRNA, piRNA, rRNA, tRNA, snRNA, snoRNA, SLRNA, SRPRNA, mRNA-like non-coding RNA, and untranslated regions in mRNA.

In another preferred example, the non-coding RNAs are selected from the group of RNA sequences as shown in SEQ ID No.: 1, 2, 3, 4, 5, 12, 13, 14 or 15.

In the second aspect of the present invention, provided is the use of a non-coding RNA sequence derived from a pathogen in the body of an animal, the non-coding RNA sequence being used (a) for the preparation of a detection reagent, a detection chip or a kit for detecting the pathogen, and (b) as a detection marker for detecting the pathogen.

In another preferred example, the detection reagent includes primers and probes.

In another preferred example, the kit includes a reagent for the specific detection of the non-coding RNA and an operation instruction.

In the third aspect of the present invention, provided is a preparation which comprises the isolated non-coding RNA sequences of the first aspect or a detection reagent to detect the isolated non-coding RNA sequences of the first aspect.

In another preferred example, the preparation includes a kit and a chip.

In the fourth aspect of the present invention, provided is an inhibitor specifically inhibiting or blocking the miRNA of the first aspect of the present invention.

In another preferred example, the inhibitor is a miRNA sponge, or an antisense nucleic acid or a small molecule compound complementary to the miRNA sequence.

In another preferred example, the inhibitor is a nucleic acid (e.g., RNA, DNA or the like) complementary to the nucleotide sequence of the miRNA of (i) or (ii).

In the fifth aspect of the present invention, provided is the use of an inhibitor, the inhibitor being an inhibitor for a non-coding RNA sequence derived from a pathogen in the body of an animal, and the inhibitor is used for the preparation of a medicament to inhibit infection or parasitism of the pathogens, or is used for the preparation of a medicament to treat an infectious disease caused by the pathogen.

In another preferred example, the inhibitor includes a compound.

In another preferred example, the inhibitor includes an antisense nucleic acid sequence.

In the sixth aspect of the present invention, provided is a method for the in vitro non-therapeutic inhibition of a pathogen, and the method includes the step of culturing the pathogen in the presence of an inhibitor, wherein the inhibitor is an inhibitor to inhibit a non-coding RNA sequence derived from the pathogen in the body of an animal.

In another preferred example, the pathogen belongs to pathogens in the body of an animal.

In the seventh aspect of the present invention, provided is a method to inhibit the pathogens infecting or parasitizing an animal by administering an inhibitor, which inhibits a non-coding RNA sequence derived from a pathogen in the body of an animal, to a subject in need thereof.

In the eighth aspect of the present invention, provided is a method to treat a pathogen infectious disease or parasitic disease by administering an inhibitor, which inhibits a non-coding RNA sequence derived from the pathogen in the body of an animal, to an animal subject in need thereof.

In the ninth aspect of the present invention, provided is an isolated or artificially constructed precursor nucleic acid sequence which can be cut in animal cells and expressed as the non-coding RNA sequence (ncRNA) of the first aspect.

In the tenth aspect of the present invention, provided is an isolated polynucleotide which can be transcribed in animal cells into an precursor nucleic acid sequence (e.g., miRNA), which can be cut in human cells and expressed as the ncRNA of the first aspect.

In another preferred example, the polynucleotide has the structure of formula I:

$$\text{Seq}_{forward}\text{-X-Seq}_{reverse} \quad \text{Formula I}$$

In formula I, $\text{Seq}_{forward}$ is a nucleotide sequence which can be expressed as the ncRNA in animal cells;

$\text{Seq}_{reverse}$ is a nucleotide sequence substantially complementary or fully complementary to $\text{Seq}_{forward}$;

X is a spacer sequence between $\text{Seq}_{forward}$ and $\text{Seq}_{reverse}$, and the spacer sequence is not complementary to $\text{Seq}_{forward}$ and $\text{Seq}_{reverse}$;

and after transferred into the human cell, the structure shown in the formula I forms a secondary structure shown in formula II:

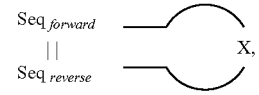

Formula II in formula II, $\text{Seq}_{forward}$, $\text{Seq}_{reverse}$ and X are defined as above, and

|| indicates a complementary base pairing relationship between $\text{Seq}_{forward}$ and $\text{Seq}_{reverse}$.

In the eleventh aspect of the present invention, provided is a vector comprising the ncRNA of the first aspect or the polynucleotide of the tenth aspect.

In the twelfth aspect of the present invention, provided is a nucleic acid chip, comprising:

a solid-phase carrier; and oligonucleotide probes orderly fixed on the solid-phase carrier, the oligonucleotide probes specifically capturing the ncRNA of the first aspect.

In the thirteenth aspect of the present invention, provided is a pharmaceutical composition including a pharmaceutically acceptable carrier and an inhibitor to specifically inhibit or block the ncRNA of the first aspect.

In another preferred example, the inhibitor is a miRNA sponge, or an antisense nucleic acid or a small molecule compound complementary to the miRNA sequence.

It should be understood that all of the various technical features described above and hereinafter (such as examples) can be combined with one another within the scope of the present invention, so as to form new or preferred technical solutions. Due to space limitations, these are no longer tired out one by one.

Figure 1:
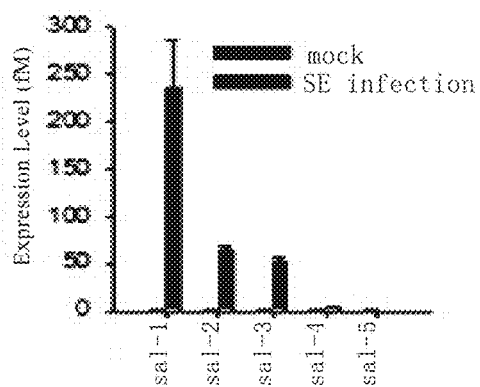
FIG. 1 shows the results of identification for ncRNA of Salmonella, an in vivo pathogen. Sals-1, 2, 3, 4, 5 represent different milRNAs detected in the same species of Salmonella, and mock means treating with PBS to simulate bacterial infection, so that none of Sals-1, 2, 3, 4, 5 is detected in the cells.
Figure 2:
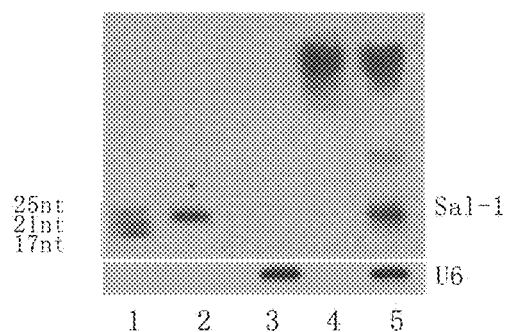
FIG. 2 shows electropherograms of ncRNA of the pathogen Salmonella. The lanes are as follows.
Figure 3:
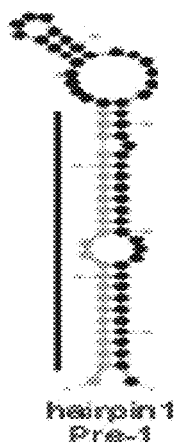

lane 1 represents a molecular weight standard;

lane 2 represents a sal-1 standard;

lane 3 represents a mock-simulated infection (PBS treated);

lane 4 represents LB-cultured *Salmonella* SE2472 (not in contact with cells); and lane 5 represents *Salmonella* SE2472-infected HT-29 cells;

FIG. 3 shows the relationship between *Salmonella* sal-1 and pre-sal-1.

Figure 4:
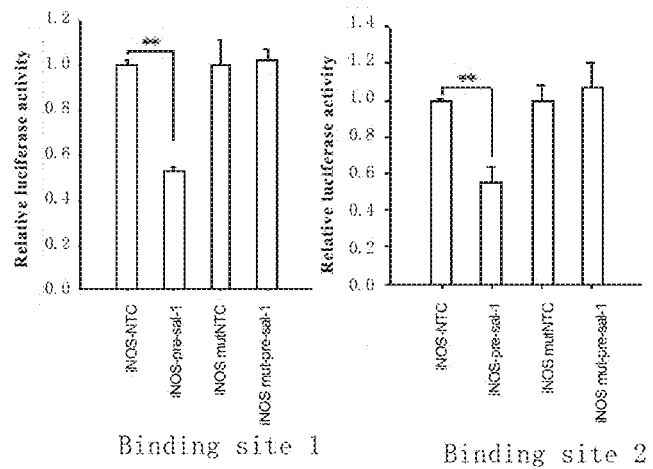

FIG. 4 shows that *Salmonella* sal-1 can regulate two target sites on iNOS.

Figure 5:
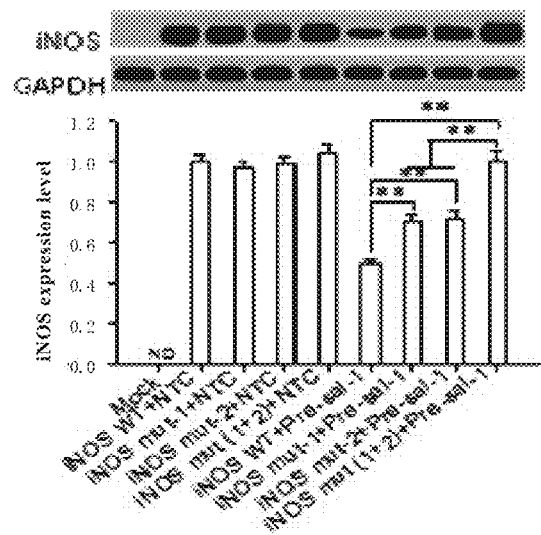

FIG. 5 shows that, with an iNOS full-length expression plasmid being transferred into an RAW264.7 cell, sal-1 can still successfully regulate the expression of iNOS.

FIGS. 6A, 6B, 6C and 6D show the regulation of *Salmonella* milRNA (sal-1) on the target gene iNOS.

FIGS. 7A, 7B, 7C, 7D and 7E show the regulation effect of Sal-1 in *Salmonella* infected mice.

FIG. 8 shows the analysis result of the H5N1 miRNA precursor stem-loop structure. The sequence of miR-H5N1-HA is shown in SEQ ID Nos.: 17, the sequence of miR-H5N1-PA-1 is shown in SEQ ID Nos.: 18, the sequence of miR-H5N1-PA-2 is shown in SEQ ID Nos.: 19.

FIGS. 9A, 9B, 9C and 9D show the quantitative PCR and northern blot detection results of the candidate miRNA in H5N1 infected cells.

FIG. 10 shows the binding sites between the miR-HA-3p and the 3' end of human and mouse PCBP2 mRNA. The sequence of Human PCBP2 3'UTR is shown in SEQ ID Nos.: 20, the sequence of first miR-HA-3p is shown in SEQ ID Nos.: 15, the sequence of Mouse PCBP2 3'UTR is shown in SEQ ID Nos.: 21, the sequence of Second miR-HA-3p is shown in SEQ ID Nos.: 22.

FIGS. 11A, 11B, 11C and 11D show that the miR-HA-3p secreted by H5N1 influenza viruses directly acts on the 3' end of PCBP2 mRNA and down-regulates the protein expression.

FIGS. 12A, 12B, 12C and 12D show that the inhibitor for miR-HA-3p brings the mice resistance against avian influenza virus H5N1.

PARTICULAR EMBODIMENTS

The present inventor is surprised in his deep and wide study to find that in vivo pathogens (including infectious microorganisms, parasitic microorganisms, symbiotic microorganisms, etc.) will release non-coding RNAs (ncRNAs), and the specific ncRNAs can serve as biomarkers of in vivo pathogens and can be used for effective detection and treatment for the in vivo pathogens, thereby significantly improving the diagnosis and treatment of microbial infectious diseases. The present invention is accomplished on this basis.

In particular, the study of the present invention indicates that the in vivo infectious microorganisms, parasitic microorganisms and symbiotic microorganisms may all participate in the physiological homeostasis and the occurrence and progression of diseases by means of ncRNAs. Different pathogens can be detected accurately and rapidly by way of the identification and detection of ncRNAs specific to different pathogens (as biomarkers of the pathogens). Furthermore, based on the ncRNAs produced using host systems by the in vivo pathogens, target inhibition and elimination can be performed with methods such as the antisense RNA technique, so as to treat microbial infectious diseases. The ncRNA-based therapy provides a new therapeutic strategy for the inhibition of microorganisms and/or microbial diseases.

Terminology

As used herein, the term "microorganism" includes various tiny organisms, such as viruses, bacteria, archaea, protists and chlamydiae. In this invention, "in vivo microorganism" refers to various microorganisms present in the bodies of hosts (human or other animals), including infectious microorganisms, parasitic microorganisms and symbiotic microorganisms. One typical class of in vivo microorganisms are pathogens causing diseases.

In this invention, according to the relationship between pathogens and host cells, the pathogens can be divided into intracellular bacteria and extracellular bacteria. The extracellular bacteria refer to the bacteria growing and reproducing in the intercellular space, blood, lymph, tissue fluid and other body fluids out of the host cells. The intracellular bacteria are divided into two kinds: facultative intracellular bacteria, which live mainly in cells for growth and reproduction in the host body and can also grow in vitro in a culture medium free of living cells; and obligate intracellular bacteria, which have to grow and reproduce in living cells, regardless of in vivo or in vitro.

As used herein, the term "milRNA" is micro-like RNA, referring to the RNA sequence from bacteria and similar to the microRNA.

As used herein, the term "sRNA" is small non-coding RNA, referring to non-coding micro RNA sequence. In this invention, sRNA includes microRNA and milRNA.

As used herein, the term "agomir" refers to a miRNA stimulant. Agomir is a specially marked and chemically modified double-stranded small RNA molecule designed according to the mature microRNA sequences, and is used to simulate the endogenous mature miRNA sequence. Generally, agomir comprises a sequence consistent with the target mature miRNA sequence and a sequence complementary to the mature miRNA sequence. The specific microRNA agomir can be introduced into the cells expressing the corresponding microRNA to simulate the action of microRNA, or be incorporated into a dual luciferase reporter system provided with miRNA binding sites, so as to verify the regulation relationship between miRNA and the target gene.

As used herein, the term "antagomir" refers to a miRNA blocker. Antagomir is a specially marked and chemically modified single-stranded small RNA designed according to the mature microRNA sequence, and is a special efficient blocker to suppress the endogenous microRNA.

Agomir and antagomir can be designed and synthesized by conventional methods according to the given short RNA sequences.

As used herein, the term "Ago2" refers to argonaute RISC catalytic component 2. It is a main component of RISC complex, and participates in short-interfering-RNA-mediated gene silencing.

iNOS refers to inducible nitric oxide synthase.

Non-Coding RNA

Non-coding RNA (ncRNA) refers to the RNA not translated into proteins, and includes various RNAs, such as rRNA, tRNA, snRNA, snoRNA, and microRNA. These RNAs are transcribed from the genome, are not translated into proteins, participate in the protein translation process, and can exercise their respective biological functions at the RNA level. For example, snRNA and snoRNA participate in the RNA splicing and RNA modification.

The non-coding RNAs are divided in terms of length into three classes: less than 50 nt, including microRNA, siRNA and piRNA; 50 nt to 500 nt, including rRNA, tRNA, snRNA, snoRNA, SLRNA, SRPRNA, etc.; and greater than 500 nt, including long mRNA-like non-coding RNA, long non-coding RNA without a polyA tail, etc.

snRNA is short for small nuclear RNA, and is also called as small nuclear RNA. Its function is to bind with protein factors to form small nuclear ribonucleoprotein particles (snRNPs) to exercise the function of mRNA splicing.

snoRNA is a small RNA first discovered in nucleoli, called as small nucleolar RNA, it was initially discovered that their biological function is to modify the rRNA. Most small nucleolar RNAs can be divided into two classes. One class is C/D box snoRNA, in which some bases of RNA are methylated. The other class is H/ACA box, in which some bases of RNA are modified with methyl uracil, it is characterized by the formation of a double-stem, added with a loop zone in the middle which provided with a box H, there is a box ACA at the tail, and the primary sequence features of box H and box ACA are loosely defined.

miRNA is a small RNA molecule complementary to the transcribed gene to mediate the gene silencing. MicroRNA is a class of 21-23 nt small RNAs, with a precursor of about 70-100 nt, forms a standard stem structure, and is transformed into 21-23 nt single-stranded RNA after processed. The function mechanism of microRNA is to complement the mRNA so as to silence or degrade the mRNA. RNAi technology developed based on the miRNA mechanism is to use small RNA similar to microRNA to silence the corresponding mRNA.

gRNA, also known as guide RNA, refers to the RNA participating in the RNA editing in eucaryotes and having a sequence complementary to the mRNA.

eRNA, an RNA molecule transcribed from an intron or non-coding DNA, can perform fine regulation for the gene transcription and translation efficiency.

Signal recognition particle RNA refers to the RNA functional molecule in cytoplasm for recognizing the mRNA containing signal peptide to determine the secretion.

pRNA refers to bacteriophage RNA. For example, the study shows that, in fi29 bacteriophage, six identical small RNA molecules are used to participate in DNA packaging by using ATP.

tmRNA refers to tRNA-like and mRNA-like complex RNAs. tmRNA is widely present in bacteria to recognize the ribosomes with incorrect translation or code reading, and also to recognize the ribosomes with delay or stalling to mediate disintegration of the ribosomes having problems.

Furthermore, the untranslated region in mRNA, including intron regions and ribosome recognition elements, such as 5'-UTR and 3'-UTR, can also be seen as a non-coding RNA.

Mechanisms

For the convenience of understanding the present invention, the inventor provides the following mechanisms. However, it should be understood that these mechanisms are not used to have any limit to the present invention.

Study of the present invention reveals that after the microorganism infects the human body, some ncRNAs of the microorganism will be secreted and enter the circulatory system, and since these ncRNAs are derived from the microorganism itself, they can be used as a diagnostic marker for the microbial infectious disease.

Typically, ncRNAs present in serum and derived from a microorganism can be used as a diagnostic marker for the microbial infectious disease. These ncRNAs specific to the pathogens in blood or serum can greatly improve the efficiency of diagnosis of the microbial infectious disease, provide great help for the treatment of the disease itself, and has important clinical significance. Moreover, intensive studies on the microorganism-derived ncRNAs will provide new clues for the mechanisms of pathogenesis or infection of such diseases.

Identification Method

The present invention further provides a general method for identifying pathogen-derived ncRNAs.

Taking the identification of ncRNAs of pathogens present in serum or blood as an example, the identification method generally comprises the steps of:

a. collecting blood or serum samples of patients infected with various microorganisms (including bacteria, archaea, viruses, *mycoplasma, chlamydia*, protists, etc.);

b. primarily screening a group of microorganism-derived sRNAs (including miRNAs) in the patient's blood or serum by means of high-throughput sequencing technology combined with bioinformatics analysis and comparison; and c. further verifying the primarily screened sRNAs using sensitive, accurate real-time fluorescent quantitative PCR to find out the respective specific serum sRNAs, derived from the microorganisms themselves, in serum of patients infected with various microorganisms and evaluate the diagnostic value of the sRNAs for the diseases themselves.

In this invention, for the identified pathogen-derived ncRNAs, feasibility of said ncRNAs as diagnostic markers can be further evaluated.

In this invention, for the identified pathogen-derived ncRNAs, the effect of said ncRNAs in the pathogen infections can be further evaluated.

A typical method is to analyze by in vitro cell infection tests. The method generally comprises the steps of:

a. infecting cells with various microorganisms (including bacteria, archaea, viruses, *mycoplasma, chlamydia*, protists, etc.), and collecting the infected cell culture fluid;

b. primarily screening a group of microorganism-derived sRNAs (including miRNAs) in the primarily screened cell culture fluid by means of high-throughput sequencing technology (Solexa sequencing technique) combined with bioinformatics analysis and comparison; and c. further verifying the primarily screened sRNAs using sensitive, accurate real-time fluorescent quantitative PCR.

The method described above provided in the present invention can identify and evaluate the specificity and accuracy of one or more ncRNAs (including miRNAs), in the body fluids and blood (or serum) of the patients with microbial infectious diseases and derived from the microorganisms themselves, for the diagnosis of microbial infectious diseases, and compare with the existing clinical diagnostic methods.

Precursor Nucleic Acid Sequence

The ncRNA (such as miRNA) can be obtained by processing a precursor nucleic acid sequence, such as precursor miRNA (pre-miRNA), which can be folded into a stable stem-loop (hairpin) structure having a general length of 50-100 bp. Said precursor miRNA can be folded into a stable stem-loop structure, and two sides of stem of the stem-loop structure contain two sequences substantially complementary to each other. Said precursor miRNA may be natural or artificially synthesized.

The precursor miRNA can be cut to generate miRNA, and said miRNA may be substantially complementary to at least a part of the sequence of the mRNA encoding the gene. As used herein, "substantially complementary" means that the nucleotide sequence is sufficiently complementary and can act upon each other in a predictable manner, e.g., forming a secondary structure (such as a stem-loop structure). Generally, at least 70% of nucleotides in two "substantially complementary" nucleotide sequences are complementary; preferably, at least 80% of nucleotides are complementary; more preferably, at least 90% of nucleotides are complementary; and further preferably, at least 95% of nucleotides are complementary, e.g., 98%, 99% or 100%. Generally, there are at most 40 non-matched nucleotides between two sufficiently complementary molecules; preferably, there are at most 30 non-matched nucleotides; more preferably, there are at most 20 non-matched nucleotides; and further preferably, there are at most 10 non-matched nucleotides, e.g., there are 1, 2, 3, 4, 5 or 8 non-matched nucleotides.

As used herein, the "stem-loop" structure, also known as the "hairpin" structure, refers to a nucleotide molecule which can form a secondary structure comprising a double-stranded region (stem) formed of two regions (on a same molecule) of this nucleotide molecule, the two regions being at two sides of the double-stranded portion; and the structure further comprises at least one "loop" structure, including non-complementary nucleotide molecules, i.e., a single-stranded region. Even if the two regions of the nucleotide molecule are not fully complementary, the double-stranded portion of the nucleotide can also maintain a double-stranded state. For example, insertion, deletion, substitution or the like may lead to a non-complementary small region or make the small region itself form a stem-loop structure or another form of secondary structure. However, the two regions can still be substantially complementary to each other and act upon each other in a predictable manner to form a double-stranded region of the stem-loop structure. The stem-loop structure is well known to a person skilled in the art, and a person skilled in the art could generally determine whether the nucleic acid can form a stem-loop structure after acquiring a nucleic acid having a nucleotide sequence of the primary structure.

Antisense Oligonucleotides

According to the milRNA sequence provided in the present invention, the antisense oligonucleotides thereof can be designed. Said antisense oligonucleotides can down-regulate expression of the corresponding milRNA in vivo. As used herein, "antisense oligonucleotides (AS-Ons or ASO)", also known as "antisense nucleotides", refer to DNA molecules or RNA molecules or analogues thereof having a length of about 18-28 nt (more specifically, about 20-26 nt).

In this invention, said "antisense oligonucleotides" further include modified antisense oligonucleotides obtained by locked nucleic acid or nucleic acid chain backbone based modification techniques. Said modification does not substantially alter the activity of antisense oligonucleotides, preferably, said modification can improve the stability, activity or therapeutic effect of antisense oligonucleotides. Locked nucleic acid (LNA) generally refers to a modification technique linking the 2'-oxygen atom with the 4'-carbon atom of ribose through a methylene bridge. LNA can extend the serum half-life of milRNA to improve affinity to the target and reduce the range and extent of off-target effects. Antisense drugs developed by the nucleic acid chain backbone based modification technique are greatly improved in terms of the solubility, resistance to nuclease degradation, etc., and are easy to be synthesized on a large scale. There are many oligonucleotide backbone modification methods, including a thio modification method, e.g., the deoxynucleotide chain is thio modified into a thiodeoxynucleotide chain. In this method, the oxygen atoms of phosphate bonds on the DNA backbone are replaced by sulphur atoms so as to be resistant to nuclease degradation. It should be understood that any modification capable of maintaining most of or all the activity of said antisense oligonucleotides are all included in the present invention.

As a preferred mode of the present invention, the antisense oligonucleotides are subjected to locked nucleic acid modification and more preferably, thio modification.

After transferring the antisense oligonucleotides of the present invention into animal (e.g., a patient with *Salmonella* infection) bodies, they can significantly down-regulate the relevant milRNA expression.

Polynucleotide Constructs

According to the milRNA sequences provided in the present invention, polynucleotide constructs which can be processed, after introduced, into milRNA capable of affecting expression of the corresponding mRNA can be designed, i.e., said polynucleotide constructs can up-regulate the level of the corresponding milRNA in vivo. Therefore, the present invention provides an isolated polynucleotide (construct), said polynucleotide (construct) can be transcribed by human cells into a precursor milRNA which can be spliced and expressed as said milRNA in human cells.

As a preferred mode of the present invention, said polynucleotide construct contains a structure shown in the formula I:

$$\text{Seq}_{forward}\text{-X-Seq}_{reverse} \qquad \text{Formula I}$$

In the formula I, $\text{Seq}_{forward}$ is a nucleotide sequence which can be expressed as said milRNA in cells, and $\text{Seq}_{reverse}$ is a nucleotide sequence substantially complementary to $\text{Seq}_{forward}$; or $\text{Seq}_{reverse}$ is a nucleotide sequence which can be expressed as said milRNA in cells, and $\text{Seq}_{forward}$ is a nucleotide sequence substantially complementary to $\text{Seq}_{reverse}$;

X is a spacer sequence between $\text{Seq}_{forward}$ and $\text{Seq}_{reverse}$, and said spacer sequence is not complementary to $\text{Seq}_{forward}$ and $\text{Seq}_{reverse}$;

and after being transferred into cells, the structure shown in the formula I forms a secondary structure shown in a formula II:

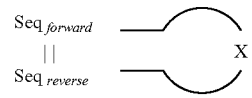

Formula II

In the formula II, $\text{Seq}_{forward}$, $\text{Seq}_{reverse}$ and X are defined above;

|| indicates a complementary base pairing relationship between $\text{Seq}_{forward}$ and $\text{Seq}_{reverse}$.

Generally, said polynucleotide constructs are located on the expression vector. Therefore, the present invention further comprises a vector containing said milRNA or said polynucleotide constructs. Said expression vector typically further contains a promoter, an origin of replication and/or a marker gene, etc. Methods well known to a person skilled in the art could be used to construct the expression vector required by the present invention. These methods include in vitro recombinant DNA technology, DNA synthesis technology, in vivo recombination technology, etc.

Said expression vector may preferably contain one or more selectable marker genes to provide a phenotypic trait for selection of transformed host cells, such as kanamycin, gentamicin, hygromycin or ampicillin resistance.

Detection Reagent, Detection Chip and Detection Kit

The present invention further provides a kit for the detection of an pathogen virus or a pathogen, comprising a detection reagent or a detection chip of the present invention. Said kit can be used to detect expression profile of the miRNA specific to a pathogen of the present invention, or used to detect an pathogen virus or a pathogen. Preferably, said kit further comprises a marker for the RNA sample and a substrate corresponding to said marker.

Furthermore, said kit may further comprise various reagents required for extraction of RNA, PCR, hybridization, colour development, etc., including but not limited to an extraction buffer, an amplification buffer, a hybridization solution, enzymes, a control solution, a developing solution, a washing liquid, antibodies, etc.

Furthermore, said kit further comprises an instruction and/or a chip image analysis software.

Nucleic Acid Chip

A nucleic acid chip (such as microRNA expression profile chip) generally contains hundreds of, thousands of or more probes, covering a variety of microRNAs, and detects contents of various microRNAs in the sample using the double-stranded homologous complementary principle. Therefore, transcription levels of microRNAs in the sample to be tested can be detected at the same time.

The miRNA sequences of the present invention can also be used to prepare the corresponding miRNA chip and further study the expression profile thereof and the regulation method of miRNAs.

In another aspect, the present invention further provides a chip to analyze the miRNA expression profile, and said chip can be used to detect a pathogen virus or a pathogen.

The miRNA chip of the present invention comprises a solid-phase carrier and oligonucleotide probes orderly fixed on said solid-phase carrier, said oligonucleotide probes comprising nucleic acid sequences related to the sequences shown in SEQ ID NOs: 1-4.

In particular, a suitable probe can be designed according to the miRNA of the present invention and is fixed on the solid-phase carrier to form an "oligonucleotide array". Said "oligonucleotide array" refers to an array having addressable locations (i.e., positions characterized by distinguishing accessible addresses), and each addressable location contains one characteristic oligonucleotide associated therewith. The oligonucleotide array can be divided into a plurality of sub-arrays as desired.

Said solid-phase carrier can use various common materials in the gene chip field, such as but not limited to nylon membranes, active group (such as an aldehyde group and an amino group) modified glass or silicon slices, unmodified glass slices, plastic slices, etc.

Said miRNA chip may be prepared by a conventional method for manufacturing biochips known in the field. For example, if the solid-phase carrier uses a modified glass or silicon slice, and the 5' end of the probe contains an amino-modified poly dT string, the oligonucleotide probes can be prepared into a solution, then the solution is applied to the modified glass or silicon slice using a spotter to arrange in a predetermined sequence or array, and then immobilize by standing overnight, so as to obtain the miRNA chip of the present invention.

The solid-phase hybridization between RNA and miRNA chip of the present invention can be carried out according to the classical method in the art, and a person skilled in the art would readily determine from experience the optimal conditions of buffers, probes, sample concentration, pre-hybridization temperature, hybridization temperature, time, etc. Alternatively, reference can be made to *Molecular Cloning, A Laboratory Manual*.

Then the information to be detected is acquired based on the information about locations of marker signals on the miRNA chip, intensity, etc. If the amplified product is labeled with fluorophores, the information to be detected can also be directly obtained by a fluorescent detection device (such as a laser confocal scanner Scanarray 3000).

Pharmaceutical Composition

The present invention further provides a pharmaceutical composition, comprising a pharmaceutically acceptable carrier and an effective amount of an inhibitor, a blocker or an antagonist for the miRNA (i.e., miR-HA-3p) of the present invention.

As used herein, the term "effective amount" or "effective dose" refers to the amount that can produce a function or activity to human and/or animals and can also be acceptable to human and/or animals.

As used herein, the "pharmaceutically acceptable" component is applicable to mammals without excessive adverse side effects (such as toxicity, irritation and allergic response), i.e., a substance with a reasonable benefit/risk ratio. The term "pharmaceutically acceptable carrier" refers to a carrier for the administration of a therapeutic agent, including various excipients and diluents.

The pharmaceutical composition of the present invention contains safe and effective amount of the active component of the present invention and a pharmaceutically acceptable carrier. Such carrier includes, but is not limited to, saline, buffer, glucose, water, glycerol, ethanol, and a combination thereof. Generally, a pharmaceutical preparation shall match the mode of administration, and the pharmaceutical composition of the present invention has a dosage form of injection, oral preparation (tablet, capsule, or oral liquid), transdermal agent, or sustained release agent. For example, preparation is performed by a conventional method using physiological saline or an aqueous solution containing glucose and other adjuvants. Said pharmaceutical composition is preferably produced under sterile conditions.

The effective amount of the active component of the present invention may vary depending on the mode of administration and the severity of the disease to be treated. A person skilled in the art could determine the selection of the preferred effective amount depending on various factors (e.g., by clinical trials). Said factors include, but not limited to, the pharmacokinetic parameters of said active component, e.g., bioavailability, metabolism, half-life, etc.; and the severity of the patient's disease to be treated, the patient's weight, the patient's immune state, the administration route, etc. Generally, when the active component of the present invention is administered at a dose of about 0.00001-50 mg/kg body weight (preferably 0.0001-10 mg/kg body weight) per day, satisfactory results can be achieved. For example, due to the urgent requirements of the treatment status, several separate doses can be administered daily, or the dosage is reduced proportionally.

The pharmaceutically acceptable carriers of the present invention include, but not limited to, water, saline, liposomes, lipids, proteins, protein-antibody conjugates, peptides, cellulose, nanogels, or a combination thereof. The choice of carriers should match the mode of administration, which would be well known to a person skilled in the art.

The present invention further provides the use of said pharmaceutical composition for the preparation of a medicament to treat a pathogen, alleviate the pathogen symptoms, and reduce the number of pathogen virus in a host animal, etc.

Use

Study of the present invention firstly reveals novel means for regulating hosts by in vivo infectious microorganisms, parasitic microorganisms and symbiotic microorganisms. Through the secretory pathway, different in vivo pathogens (such as in vivo infectious microorganisms, parasitic microorganisms and symbiotic microorganisms) present non-coding RNAs (ncRNAs) produced thereby to the host cells, and affect the immune system of the host "by means of" host proteins, thereby helping the in vivo pathogens live in the body of host. Therefore, it is a new way to inhibit microbial infections and treat microbial diseases by interfering with or inhibiting the pathogen-specific ncRNAs.

Based on the present invention, it is found to use a pathogen-specific ncRNA as a detection (or diagnosis) marker and as a therapeutic target.

Taking a *Salmonella* bacterium as example, the *Salmonella* bacterium presents the non-coding RNAs (ncRNAs) encoded by the bacterium itself into a host cell, generates milRNAs similar to microRNAs by means of a microRNA splicing system in the cell, and regulates the immune system (such as iNOS) with milRNAs, which is then utilized by the bacterium so as to protect itself from being cleared by the host. Adsorbing milRNAs using milRNA inhibitors can effectively inhibit the survival ability of the bacterium in the cell, leading to a reduced survival ability of the bacterium, and therefore the inhibitors can be used in the treatment of bacterial infections.

Taking avian influenza as an example, the parasitic microorganism avian influenza virus H5N1 secretes miR-HA-3p, and the miR-HA-3p acts on PCBP2 to inhibit the negative regulation on the RIG-I/MAVS pathway and eventually lead to an increase in the cytokine production and an aggravation in the body inflammatory response. The mice treated with antagomir-HA-3p (an inhibitor of miR-HA-3p) show a stronger resistance to H5N1, and have less weight loss and longer survival time after infection. Since miR-HA-3p is strongly conservative in the virus strain isolated from H5N1, it can serve as an important factor in the treatment of H5N1. Antagomir-HA-3p can serve as an effective therapy for the remission of H5N1 virus.

The main advantages of the present invention include:

(a) providing a simple, fast and accurate new method detecting infections of pathogens, and (b) providing a new way to inhibit microbial infections and treat microbial diseases.

The present invention is further illustrated in connection with particular embodiments as follows. It should be understood that these embodiments are merely illustrative of the invention and are not intended to limit the scope of the present invention. In the case of specific conditions for the experimental method being not specified in the following examples, generally conventional conditions are followed, such as the conditions described in Sambrook et al., *Molecular Cloning: A Laboratory Manual* (New York: Cold Spring Harbour Laboratory Press, 1989), or the conditions recommended by the manufacturer are followed. All percentages and parts are weight percentages and weight parts unless otherwise indicated.

Example 1

Identification and Application of *Salmonella* ncRNA

In this example, the in vivo pathogen *Salmonella* is studied, the results show that *Salmonella* can produce milRNA (a kind of ncRNA) by means of using the host, and effective detection and treatment for *Salmonella* infections can be performed through targeting the ncRNA.

(1) Screening of milRNA in Bacterium Infected Cells

Isolation and streaking for *Salmonella* strains are performed on an LB plate using an inoculating loop, medium-sized colonies are picked and inoculated onto a LB liquid medium, cultured at 37° C. overnight, then centrifuged to remove the LB medium, and the strains are resuspended with RPMI-1640+10% FBS medium.

One day before the infection with bacteria, human intestinal epithelial cells HT-29 digested with trypsin are plated in a cell culture dish, and cultured at 37° C. in a 5% CO2 incubator.

Cells are infected at a ratio of MOI (5-10:1), washed with PBS to remove the bacteria that have not been infected and entered the cells 2 hours after infection, then cultured with gentamicin-containing RPMI-1640+10% FBS, washed with PBS three times after cultured overnight, and cells are lysed with 0.1% PBST (PBS+Triton X-100), and filtered with 0.22 μm filter to remove the bacteria. Through the above treatment, the bacteria that have not entered cells and remain in cells can be completely removed.

Then total RNA is extracted from the lysate with Trizol LS, and subjected to deep sequencing by Solexa, the tested data are analyzed, and *Salmonella* specific small RNA fragments are identified.

1.1 Identification for milRNA

The fragments obtained by Solexa sequencing are analyzed, high-copy milRNA fragment sequences are screened, and quantitative PCR detection probes and northern blot detection probes are designed and synthesized for these sequences.

1.2 Northern Blot Detection

Total RNA of the *Salmonella* strain cultured with LB and cytoplasm total RNA of the cells infected with *salmonella* are extracted respectively with Trizol LS reagent, resuspended with 1×RNA loading buffer (Takara), then subjected to electrophoresis with 15% TBE-Urea polyacrylamide-gelelectrophoresis (PAGE), and the RNAs are transferred and printed on a nylon membrane after electrophoresis, glued by ultraviolet (UV), then hybridized with a digoxin (DIG) labeled probe, and the expression of milRNA is analyzed.

1.3 Fluorescent Quantitative PCR Assay

Total RNA of the *Salmonella* strain cultured with LB and cytoplasm total RNA of the cells infected with *salmonella* are extracted respectively with Trizol LS reagent, then dissolved with ultrapure water treated with DEPC, firstly reverse-transcribed into cDNA with the downstream primer of a probe, then subjected to quantitative PCR amplification with a synthesized probe (ABI), and the content of milRNA in each sample after amplification is analyzed.

Results

Experimental results are as shown in FIGS. 1, 2 and 3.

Detection is performed using northern blot and qRT-PC, the results of FIGS. 1 and 2 show that small RNAs of 19-30 nt (known as milRNA in the present invention) appear only after the *Salmonella* strain infects cells, and the present invention selects milRNA (sal-1) to make a comprehensive and in-depth study.

The sequence condition of milRNA (sal-1) on the genome of *Salmonella* is analyzed using a biological software, and the detailed results are shown in FIG. 3. FIG. 3 shows that the ncRNA where milRNA (sal-1) is located can be folded into pre-sal-1.

Partial ncRNA sequences from *Salmonella* are as follows:

Sal-1:
(SEQ ID No.: 1)
UGUGGGCACUCGAAGAUACGGAUU

Sal-2:
(SEQ ID No.: 2)
AUGCGAGAGUAGGGAACUGCCAGGCAU

Sal-3:
(SEQ ID No.: 3)
UCCUCUGUAGUUCAGUCGGUAGAACGGC

Sal-4:
(SEQ ID No.: 4)
GAAGGUGGCGGAAUUGGUAGACG

Sal-5:
(SEQ ID No.: 5)
GCCCGGAUGGUGGAAUCGGUA

The sequence of Pre-sal-1 is:
(SEQ ID No.: 6)
5'-TGTGGGCACTCGAAGATACGGATTCTTAACGTCCTAGGACG
AAAAATGAATACCAAGTCTCAAGAGTGAACACG-3'

(2) The Ability of milRNA Inhibitors to Inhibit the Bacteria Infecting Hosts 2.1 In Vitro Test In this test, for the identified *Salmonella* specific sal-1, the correlation between it and the target gene inducible nitric oxide synthase (iNOS) is studied.

A target site region capable of binding with milRNA is amplified by PCR, double-digested by Spe I+Hind III and inserted into a pMIR-REPORT luciferase vector (purchased from Shanghai Innovation Biotechnology Co., Ltd.) to construct a recombinant plasmid (iNOS). In addition, the milRNA binding site of the above constructed recombinant plasmid is mutated to construct a recombinant mutant plasmid (iNOS mut).

Furthermore, the precursor of milRNA is loaded to an expression vector with CMV as a promoter, to construct a vector (pre-sal-1) overexpressing milRNA.

The milRNA control plasmid or pre-sal-1 and iNOS or iNOS mut are co-transfected into HEK-293T cells, and the reporter gene is detected, with the β-gal plasmid as a reference.

The particular result is shown in FIG. 4. The result of Luciferase in FIG. 4 shows that sal-1 can regulate both of the two target sites on iNOS, so as to down-regulate iNOS.

2.2 Western Blot

The full-length wild-type iNOS gene is cloned into an eukaryotic expression plasmid to construct a recombinant plasmid expressing iNOS (iNOS WT) for iNOS expression, and furthermore mutation for the milRNA binding sites (synonymous mutation, changing only the base sequence without changing the amino acid sequence) is performed to construct the plasmid expressing iNOS (iNOS MUT) for the expression of mutated iNOS. The pre-sal-1 is co-transfected with iNOS WT and iNOS MUT respectively into mouse RAW264.7 cells (these cells do not express iNOS unless they are stimulated) for expression to detect the regulatory capacity of milRNA on iNOS.

The particular result is shown in FIG. 5. The result in FIG. 5 shows that after transferring iNOS full-length expression plasmids into RAW264.7 cells, sal-1 can likewise successfully regulate the iNOS expression (down-regulation).

2.3 Cell Infection Test

HT-29 cells are plated in a 24-well plate one day before infected with a *Salmonella* strain, and on the next day transfected with anti-sal-1 using lipofectin 2000, and in 24 h after transfection with anti-sal-1, the cells are infected with the *Salmonella* strain in an MOI (5-10:1) with the control group using random sequences, and the survival ability of intracellular bacteria is detected in 24 h after infection.

Figure 6:
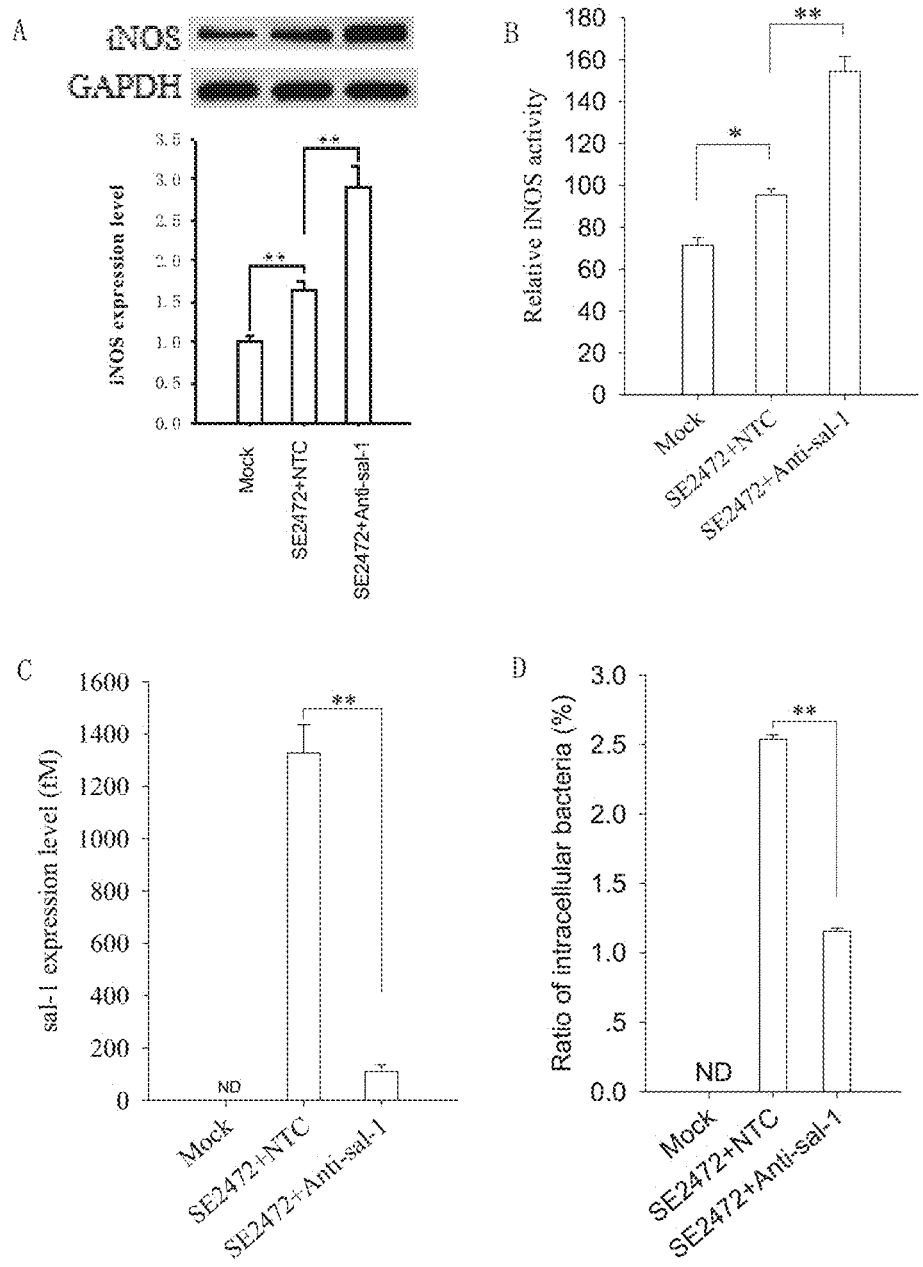

The antisense nucleic acids have sequences (5' to 3') as follows:

anti-sal-1:
(SEQ ID NO.: 7)
AAUCCGUAUCUUCGAGUGCCCACA anti-sal-2:
(SEQ ID NO.: 8)
AUGCCUGGCAGUUCCCUACUCUCGCAU anti-sal-3:
(SEQ ID NO.: 9)
GCCGUUCUACCGACUGAACUACAGAGGA anti-sal-4:
(SEQ ID NO.: 10)
CGUCUACCAAUUCCGCCACCUUC anti-sal-5:
(SEQ ID NO.: 11)
UACCGAUUCCACCAUCCGGGC The detailed results are shown in FIG. 6. FIG. 6 shows that, with human intestinal epithelial cells (HT-29) as a model of infection, when the HT-29 cells are infected with a *Salmonella* strain, the cells are transfected with the sal-1 inhibitor (anti-sal-1), then the expression of iNOS is analyzed and activity detection is performed, and the survival rate of the *Salmonella* strain in cells is analyzed. The iNOS expression of the *Salmonella* strain infected with the sal-1 inhibitor is further increased by about 2.8-fold (FIG. 6A); and the iNOS activity is also increased accordingly by about 2.3-fold (FIG. 6B). However, the sal-1 expression level is down-regulated by about 90% (FIG. 6C), and the number of *Salmonella* in cells after the infection is also decreased to 45% (FIG. 6D).

2.4 In Vivo Experiment

The pre-sal-1 sequence after enzyme digestion is inserted into a conventional lentivirus vector to package the lentivirus overexpressing milRNA.

The sequence complementarily binding with milRNA is constructed into a sponge capable of binding with milRNA (containing 3 repetitions of complementary fragment) by means of genetic engineering, and then the milRNA sponge is also inserted into the lentivirus vector to package the lentivirus capable of adsorbing milRNA.

In addition, since iNOS can also be expressed in a body of mouse, in order to verify the regulatory function of milRNA on iNOS, the present inventor constructs an expression plasmid with all the binding sites of milRNA on mouse iNOS being mutated, then this plasmid is also enzymatically digested and then inserted into the lentivirus vector to package the lentivirus capable of overexpressing the mouse iNOS.

Taking 6-8 weeks old BALA/C mice as experimental subjects, the effect of the up- or down-regulation of milRNA on the expression of iNOS is analyzed, and the invasion in mice is compared. Taking 6-8 weeks female BALB/C mice as infection models, the lentivirus overexpressing milRNA (sal-1), the lentivirus overexpressing iNOS (the sal-1 binding site of mouse iNOS is subjected to the amino acid synonymous mutation to result in a capacity of not binding or lowly binding with sal-1), and the lentivirus specifically adsorbing milRNA (sal-1) sponge, are packaged using recombinant lentivirus respectively. The experiment is divided into 8 groups: mock; *Salmonella* (SE2472); lenti-NTC+SE2472; lenti-sal-1+SE2472; lenti-sal-1 sponge+SE2472; lenti-NTC+iNOS MUT SE2472; lenti-sal-1+iNOS MUT SE2472; and lenti-sal-1 sponge+iNOS MUT SE2472.

Figure 7:
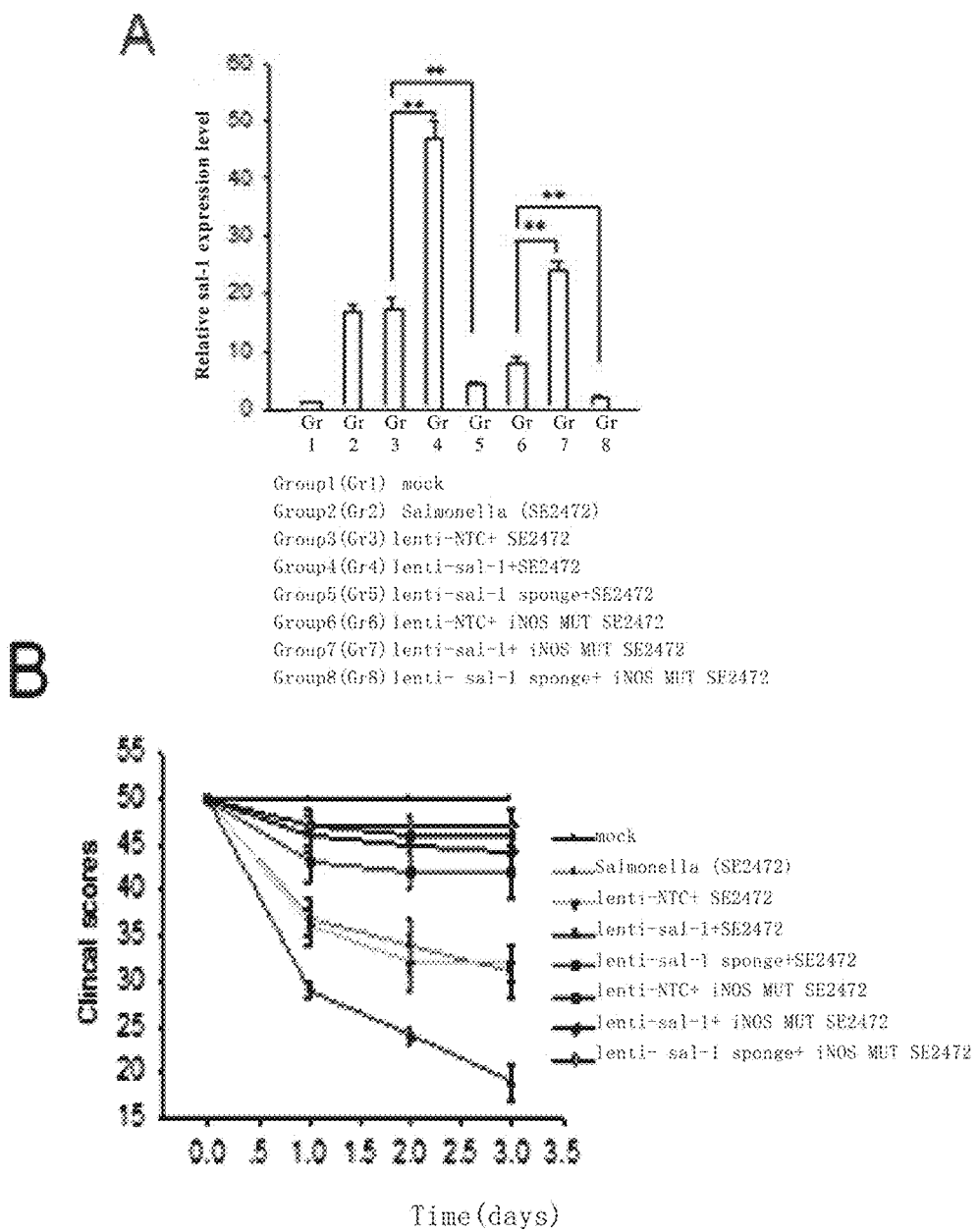

The detailed results are shown in FIG. 7. FIG. 7 shows the expression of sal-1 in the mouse model.

The result of FIG. 7A shows that, after the mice are infected with *Salmonella* SE2472, the expression of sal-1 is increased, the expression of sal-1 in the group lenti-sal-1+SE2472 is further increased, and the expression level of sal-1 in the group lenti-sal-1 sponge+SE2472 is decreased due to the adsorption by the sal-1 sponge (an inhibitor for sal-1). When the sal-1 binding sites of iNOS in mice are subjected to synonymous mutation and then packaged into lentivirus to re-infect the mice, the sal-1 is decreased (because the expression of mutant iNOS affects the survival ability of bacteria in mice, and the number is decreased), and the expression of sal-1 in the group lenti-sal-1+iNOS MUT SE2472 shows a certain scale of response expression, while the expression of sal-1 in the group lenti-sal-1 sponge+iNOS MUT SE2472 is further decreased.

FIG. 7B indicates that the eight groups of mice have changed clinical symptoms when infected with SE2472, and these changes are consistent with the changes in bacterial infection symptoms caused by the above changes of sal-1.

FIGS. 7C and 7D show the change in expression of iNOS in the eight groups, wherein in the *Salmonella* SE2472 infection, the expression difference of iNOS is not significant, and only when the sal-1 sponge is used, the expression of iNOS can obviously achieve a response expression. This clearly indicates that sal-1 regulates the expression of iNOS, and when iNOS is subjected to synonymous mutation, it can be seen that the expression of iNOS is further increased, and is not regulated by sal-1. The results show that sal-1 can indeed regulate the expression of iNOS.

In FIG. 7E, the bacterial contents in the tissues (*Salmonella* removed from the enteric cavity) of large intestines of mice in the eight groups are detected. The up-regulated expression of sal-1 can promote the infection ability of bacteria in the intestinal tissue, and after the sal-1 is adsorbed and removed by the sponge, the infection ability of bacteria are decreased. In the iNOS synonymous mutation group, sal-1 does not play a regulatory role. All the results indicate that sal-1 regulates iNOS, and affects the infection and survival ability of the bacteria in the body of host through iNOS.

The result of the example of the present invention indicates that the *Salmonella* bacterium presents the non-coding RNAs (ncRNAs) encoded by the bacterium itself into a host cell, generates milRNAs similar to microRNAs by means of a microRNA splicing system in the cell, and regulates the immune system (such as iNOS) with milRNAs, which is then utilized by the bacterium so as to protect itself from being cleared by the host. In the present invention, the milRNA inhibitor can effectively inhibit the survival ability of the bacteria in cells through adsorbing milRNA, leading to a reduced survival ability of *Salmonella*, therefore the inhibitor can be used in the treatment of bacterial infections.

(3) Use of *Salmonella* milRNA

The milRNA of the present invention is used for (a) the preparation of a reagent, a detecting chip or a kit for detecting *Salmonella* infections; or (b) the preparation of a regulator for regulating the iNOS expression or activity.

The nucleic acid chip for detecting *Salmonella* infections comprises: a solid-phase carrier; and oligonucleotide probes orderly fixed on the said solid-phase carrier, and the said oligonucleotide probes specifically capture the milRNA of the present invention.

The nucleic acid chip for detecting *Salmonella* infections of the present invention can screen with a high-throughput milRNA probes that stably change in serum, and furthermore predict and diagnose diseases through the overall change of milRNA in serum. The inventor firstly determines milRNA with no less than one copy in serum by the sequencing or quantitative PCR method, then synthesize reverse complementary probes of these milRNAs, and then spot these probes on a 75×25 mm chemically modified glass slide by a chip spotter SmartArray™. The samples spotted to the chip further include U6 as an interior label, tRNA, an artificially prepared external label with 30-base length, a positive control Hex, etc. The whole dot array is divided into four sub-arrays, each of which has 23 rows and 21 columns, with dot interval of 185 μm and dot diameter of about 130 μm, and each probe is replicated three times.

The chip operation process is as follows: (1) extraction of total RNA from serum/plasma, and detection of the mass of total RNA by formaldehyde denaturing gel electrophoresis; (2) isolation of milRNA: taking 50-100 μg of total RNA, and isolating milRNA with Ambion's miRNA Isolation Kit (Cat #. 1560); (3) fluorescence labelling of milRNA samples: performing fluorescence labelling with T4 RNA ligase labelling method, then precipitating with absolute ethyl alcohol, and blow-drying for chip hybridization; (4) hybridization and washing: dissolving the RNA in a 16 μL hybridization solution (15% formamide; 0.2% SDS; 3×SSC; and 50×Denhardt's solution), and hybridizing overnight at 42° C., and after hybridization, washing in a liquid containing 0.2% SDS and 2×SSC at about 42° C. for 4 minutes, then washing in 0.2×SSC at room temperature for 4 minutes, and drying the glass slide for scanning; (5) chip scanning: scanning the chip using a LuxScan 10K/A dual-channel laser scanner; and (6) data extraction and analysis: analyzing the chip image using a LuxScan 3.0 image analysis software, converting the image signals into digital signals, and finally choosing differentially expressed genes by SAM analysis.

The serum/plasma milRNA probes that show a large extent of differential expressions between *Salmonella* infections and under the normal physiological state by verification with both quantitative PCR technology and biochip technology can be used for the preparation of biochips, and the method is the same as above. Being compared with traditional chips, this chip has no significant improvement on the manufacture process and operation procedure, but it simplifies the probe library, which will greatly reduce the production cost and time, and can be easily prepared. It also increases the specificity and practicability of the chip. When this chip is put into practice, it can detect diseases at an early stage and help guide diagnosis and treatment, which only needs the patient's serum/plasma without any other tissue.

In addition, the nucleic acid chip of the present invention is used to prepare a kit for detecting *Salmonella* infections. The kit for detecting *Salmonella* infections contains the nucleic acid chip of the present invention or the milRNA of the present invention.

The production process and operation procedure of the milRNA kit for the diagnosis and efficacy evaluation for *Salmonella* infections as well as the screening and efficacy evaluation of pharmaceutically active ingredients are based on quantitative and semi-quantitative PCR technology and biochip technology.

Firstly, milRNAs with no less than one copy in serum are determined by the sequencing or quantitative PCR method.

Then the serum/plasma milRNAs that show significant expression differences between under a diseased state and normal physiological state are screened by quantitative PCR technology and biochip technology, as an indicator for predicting whether a *Salmonella* infection occurs and diagnosing the disease degree. Finally, the number of corresponding serum/plasma milRNAs is screened, and this is the optimized simplification made on the basis of the chip probe library. This kit comprises serum/plasma milRNA primers, Taq polymerase, dNTP and other reagents. The value of this kit is that, it only needs serum/plasma without other tissue samples, and can be used to detect the change trend of milRNA with the simplest probe library and then the likelihood of *Salmonella* infection occurrence can be predicted or the pathologic stages of *Salmonella* infections can be diagnosed according to this change trend. Therefore, this kit can be put into practice to increase the possibility of detecting *Salmonella* infections at an early stage to help guide diagnosis and treatment.

Example 2

Identification and Application of *Neisseria gonorrhoeae* ncRNA

In this example, the in vivo pathogen *Neisseria gonorrhoeae* is studied, and the results show that *Neisseria gonorrhoeae* secrets ncRNA and is involved in the physiological homeostasis and the occurrence and development of disease via ncRNA. The ncRNA, as a biomarker of *Neisseria gonorrhoeae*, can be used in the effective diagnosis of microbial infectious diseases.

(1) Identification of ncRNA Secreted by *Neisseria gonorrhoeae*

Firstly, strains of *Neisseria gonorrhoeae* are screened by plate streaking in the same way as in example 1.

Then Solexa deep sequencing is performed, and the sequencing data are analyzed, discovering the *Neisseria gonorrhoeae* specific ncRNA, with the sequence of GUAUCCCAUCCUCGUCGCCA (SEQ ID No.: 12).

The fragments obtained by Solexa sequencing are analyzed, high-copy ncRNA fragment sequences are screened out, and quantitative PCR probes and northern blot detection probes are designed and synthesized for these sequences. The quantitative PCR detection operation is substantially the same as in example 1. The difference is that the extracted total RNA is the total RNA of *Neisseria gonorrhoeae*.

The Northern blot detection operation is substantially the same as in example 1.

Results

The Northern blot and qPCR detection results show that *Neisseria gonorrhoeae* can secrete ncRNA, and the ncRNA can be folded into a stem-loop structure.

(2) Application of a ncRNA-Targeting Inhibitor to Inhibit Bacteria Infecting a Host The reporter gene of ncRNA secreted by *Neisseria gonorrhoeae* is analyzed using a biological software, with the specific operation as described in example 1. The luciferase result indicates that the ncRNA secreted by *Neisseria gonorrhoeae* can regulate metabolic enzymes.

Taking human intestinal epithelial cells (HT-29) as the infection model, when HT-29 cells are infected by *Neisseria gonorrhoeae*, an inhibitor of the reporter gene (for the antisense nucleic acid of SEQ ID NO.: 12) is transfected, then the expression of enzymes and activity detection are analyzed, and the survival rate of *Neisseria gonorrhoeae* in cells is analyzed, with the specific operation generally in the same way as in example 1. After the treatment for the antisense nucleic acid of SEQ ID NO.: 12, the number of *Neisseria gonorrhoeae* in the infected cells accordingly decreases by not less than 35%.

Taking 6-8 weeks old BALA/C mice as experimental subjects, the effect of the up- or down-regulation of ncRNA in *Neisseria gonorrhoeae* on the expression of metabolic enzymes is analyzed, and the invasion on mice is compared. Taking 6-8 weeks old female BALB/C mice as the infection model, lentivirus overexpressing *Neisseria gonorrhoeae* ncRNA, lentivirus overexpressing metabolic enzymes and lentivirus with sponge specifically absorbing *Neisseria gonorrhoeae* ncRNA are packaged respectively using recombinant lentivirus. The specific operation is as described in example 1. The result indicates that the *Neisseria gonorrhoeae* ncRNA regulates the expression of metabolic enzymes, and when the metabolic enzymes are subjected to synonymous mutation, the expression further increases and is not regulated by *Neisseria gonorrhoeae* ncRNA, showing that *Neisseria gonorrhoeae* ncRNA can actually regulate the expression of metabolic enzymes. *Neisseria gonorrhoeae* ncRNA affects the invasion and survival ability of bacteria in the body of host by regulating the metabolic enzymes.

Example 3

Identification and Application of ncRNA of Avian Influenza Virus

This example studies the ncRNA of avian influenza virus, and confirms that an inhibitor for the ncRNA of avian influenza virus H5N1 (i e, miR-HA-3p) can effectively decrease the death rate caused by H5N1 virus.

In this example, the main reagents include:
agomir, a random sequence, used as a control;
agomir-HA-3p, the ncRNA of H5N1;
and antagomir, representing an inhibitor for avian influenza ncRNA. Herein, antagomir-HA-3p is an inhibitor specific to miR-HA-3p, and has a sequence which is an antisense sequence fully complementary to miR-HA-3p.

miR-HA-3p represents specific ncRNAs derived from avian influenza H5N1, with the sequences of:

| Name | Sequence (5'-3') | Length (nt) | SEQ ID NO.: |
|---|---|---|---|
| miR-HA-3p-1 | AGGACUAUUUG GAGCUAUAGCA | 22 | 13 |
| miR-HA-3p-2 | GGACUAUUUGG AGCUAUAGCAG | 22 | 14 |
| miR-HA-3p-3 | GAGGACUAUUU GGAGCUAUAGC | 22 | 15 | wherein, the core sequence of the three kinds of ncRNA is GGACUAUUUGGAGCUAUAGC (SEQ ID NO.: 16).

Agomir-HA-3p (M) represents an RNA sequence having a length of 22 nt, of which the core sequence is modified.

(1) The Parasitic Microorganism Avian Influenza Virus H5N1 Secretes miR-HA-3p

Firstly, the stem-loop structure of the candidate miRNA is analyzed using a biological software.

The particular results are shown in FIG. 8. FIG. 8 shows the predicted secondary structure of the stem-loop structure of the H5N1 miRNA precursor. The prediction is carried out by Mfold, and the 5' and 3' ends of the predicted mature miRNA are respectively marked with red and blue colors. The result indicates that, in the three predicted precursors, one is encoded by the HA fragment, and the other two are encoded by the PA fragment. Each candidate miRNA can be folded into a stable specific hairpin structure.

Then quantitative PCR detection probe and northern blot detection probe are designed and synthesized for the candidate miRNA sequence, and the expression level of the candidate miRNA in the H5N1 infected cells is detected. The specific operations of the quantitative PCR detection method and the northern blot detection method are as described in example 1.

Figure 9:
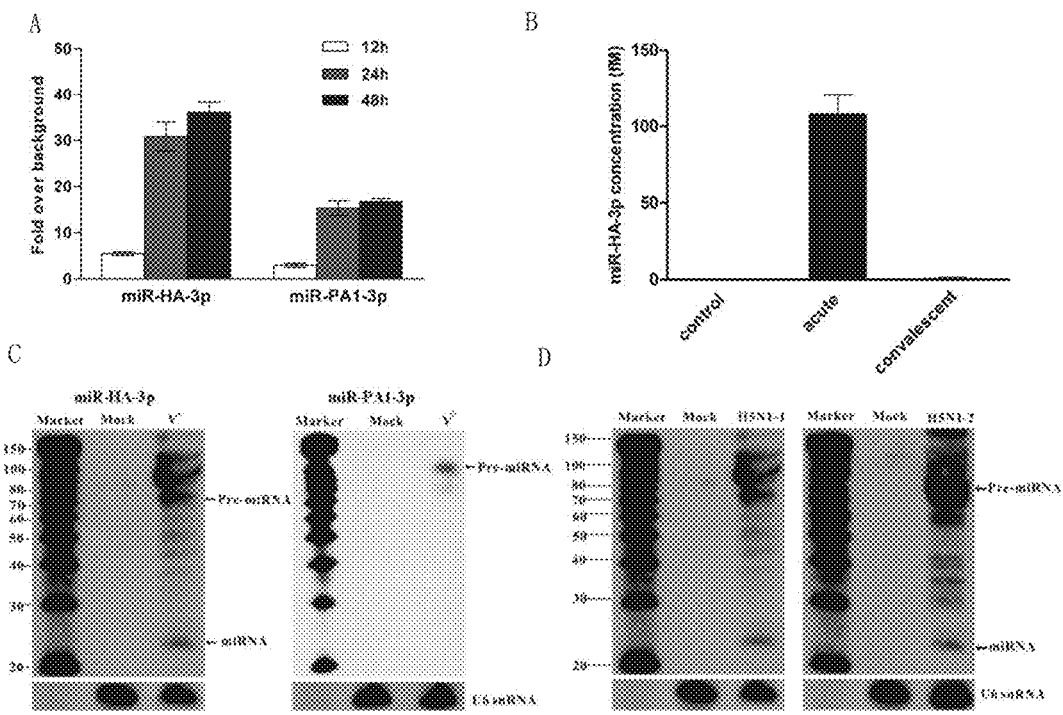

The particular result is shown in FIG. 9.

FIG. 9 shows the quantitative PCR and northern blot detection results of the candidate miRNA in H5N1 infected cells.

FIG. 9A shows the expression levels of miR-HA-3p and miR-PA1-3p in A549 cells at different time points. It can be seen from FIG. 9A that the expression levels of the two kinds of miRNA are gradually increased during the infection. The results of real-time quantitative PCR show that, at each time point, the expression level of miR-HA-3p is higher than that of miR-PA1-3p.

FIG. 9B shows the expression levels of miR-HA-3p in the serum of a patient at severe H5N1 infection stage and in convalescent state. It can be seen from FIG. 9B that the expression level of miR-HA-3p in the serum of the patient at the severe infection stage is very high, and after the viral infection is decreased, miR-HA-3p is barely detectable.

The results of FIGS. 9A and 9B indicate that, after infecting host cells, H5N1 will secrete a special small molecule miR-HA-3p that will enter the in vivo circulation of the host, and the expression level of miR-HA-3p is in direct correlation with the viral infection degree.

FIGS. 9C and 9D show the northern blot detection results of miR-HA-3p and miR-PA1-3p in the H5N1 infected cells.

FIG. 9C shows the northern blot detection results of miR-HA-3p and miR-PA1-3p in the H5N1 infected A549 cells. It can be seen from FIG. 9C that, with U6 as a control, miR-HA-3p precursor miRNA with a length of about 80 nt and mature miR-HA-3p of 22 nt can be quickly detected from the H5N1 infected A549 cells. The precursor miR-PA1-3p RNA of about 100-nt can be detected, while the mature miR-PA1-3p cannot be detected.

FIG. 9D shows the northern blot detection results of miR-HA-3p in H5N1 IAV isolated strains. It can be seen from FIG. 9D that small RNA fragments (<200) are extracted from the H5N1 infected A549 cells, and these fragments are hybridized with probes, with the results showing that both the two H5N1 IAV isolated strains can produce miR-HA-3p, and the results show that miR-HA-3p does not only exist in specific H5N1 influenza virus.

(2) miR-HA-3p Secreted by H5N1 Influenza Virus Acts Directly on the 3' End of PCBP2 mRNA and Down-Regulates the Protein Expression.

Firstly, target sites of miR-HA-3p are analyzed using a biological software. Then the target sites of miR-HA-3p are confirmed and analyzed by reporter gene detecting luciferase method, with specific operation steps as described in example 1.

Figure 10:
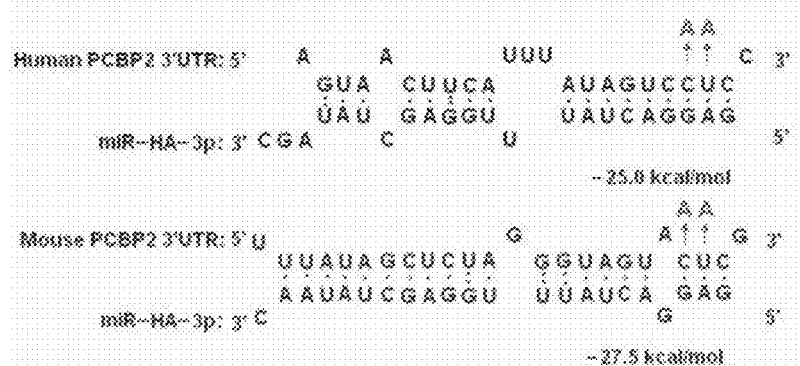

The particular results are shown in FIG. 10. FIG. 10 shows the predicted binding sites between the miR-HA-3p and the 3' end of human and mouse PCBP2 mRNA. It can be seen from the results of FIG. 10 that PCBP2 mRNA is a potential target site of miR-HA-3p. Similar results are obtained in humans and mice. PCBP2 belongs to the nucleo-protein E family, and is related with the MAV-mediated antiviral effect. H5N1 can enhance the MAV mediated anti-virus process by silencing PCBP2, so as to cause an excessive immune response or cytokine storm in the H5N1 invasion process.

Then, using the luciferase activity detection method, the western blotting detection method and the quantitative PCR detection method, the changes in luciferase activity, protein level and protein mRNA level of the HEK293T cells transfected with wild type and mutant type human and mouse PCBP2 genes after being respectively treated with agomir, agomir-HA-3p and agomir-HA-3p (M) are analyzed.

Figure 11:
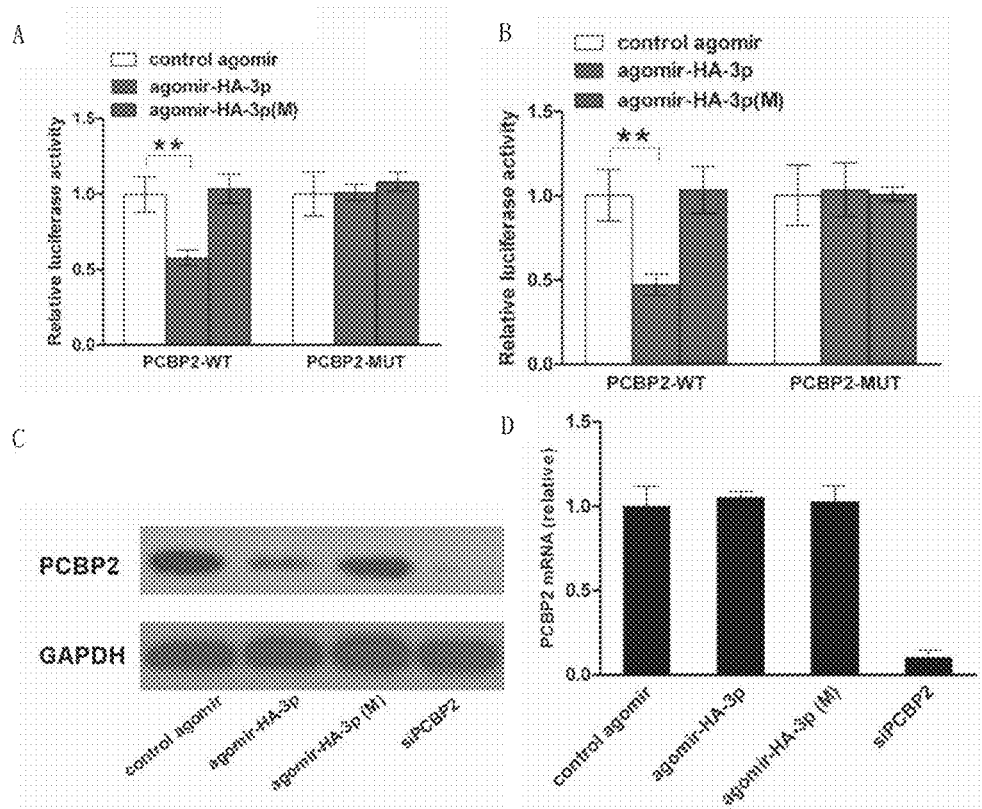

The particular result is as described in FIG. 11. FIG. 11A shows the change in luciferase activity after the HEK293T cells transfected with wild type and mutant type human PCBP2 gene after being respectively treated with agomir, agomir-HA-3p (an miR-HA-3p stimulant), and agomir-HA-3p (M) (a mutant miR-HA-3p stimulant). FIG. 11B shows the change in luciferase activity after the HEK293T cells transfected with wild type and mutant type mouse PCBP2 gene are treated with agomir, agomir-HA-3p and agomir-HA-3p (M) respectively.

It can be seen from the results of FIGS. 11A and 11B that agomir-HA-3p can significantly down-regulate the expression level of 3' end luciferase of the wild type PCBP2. However, agomir-HA-3p (M) has no such effect. As a comparison test, the sample is changed to HEK293T cells transfected with PCBP2 with luciferase gene carried on the 3' end, and both the two stimulants do not affect the luciferase activity in the comparison test. The results indicate that miR-HA-3p can directly act on the 3' end of PCBP2 mRNA.

FIG. 11C shows the Western blotting analysis results of the PCBP2 protein levels in A549 cells treated with agomir, agomir-HA-3p and agomir-HA-3p (M). It can be seen from FIG. 11C that siPCBP2 is an RNAi system to silence PCBP2 gene, and after the A549 cells are transfected with agomir-HA-3p as control, the expression of PCBP2 detected by Western blot is significantly suppressed, while the expression of PCBP2 in cells transfected with agomir-HA-3p (M) shows no significant change.

FIG. 11D shows the expression levels of PCBP2 mRNA in A549 cells after treated with agomir, agomir-HA-3p and agomir-HA-3p (M). It can be seen from FIG. 11D that the ability to down-regulate the PCBP2 of miR-HA-3p is equivalent to that of siPCBP2. The agomir-HA-3p treated group has no significant difference from the agomir group, with the result indicating that miR-HA-3p plays a role in inhibiting the PCBP2 protein translation.

In summary, miR-HA-3p secreted by H5N1 influenza virus directly acts on the 3' end of PCBP2 mRNA and down-regulates the protein expression.

(3). The miR-HA-3p Inhibitor Brings Mice the Resistance Against H5N1.

Female BALB/C mice are divided into two groups and intranasally inoculated respectively with a lethal dose of H5N1 and mutant strain of H5N1, and then their body weights, mortalities, viral replication and cytokine polymer are detected.

8 hours after virus invasion, the mice are respectively injected with antagomir-HA-3p and antagomir for five consecutive days. The particular results are shown in FIG. 12.

FIGS. 12A and 12B show the death rates of mice inoculated with H5N1 or the mutant strain under different treatment conditions. FIGS. 12C and 12D show the degree of weight loss of mice inoculated with H5N1 or the mutant strain under different treatment conditions.

Figure 12:
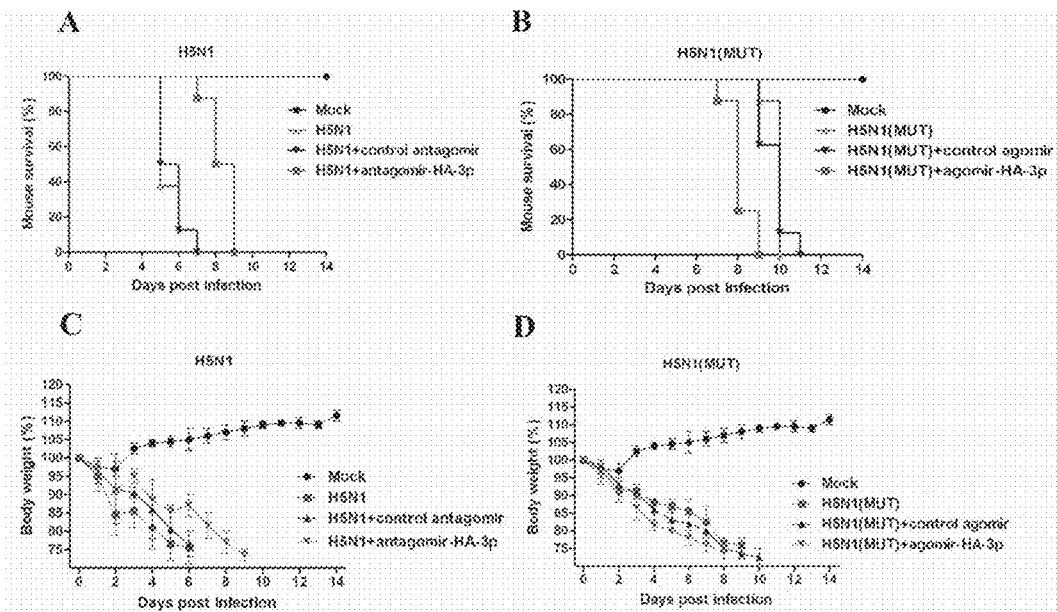

It can be seen from FIG. 12 that, seven days after inoculation, the mice inoculated with H5N1 has a death rate of 100% (FIG. 12A), accompanied with weight loss of not less than 20% (see FIG. 12C). The treatment with antagomir forms no effect on the death and weight loss of mice; however, the mice in the antagomir-HA-3p treated group show certain weight loss after seven days, and the death rate thereof is only about 10%. This phenomenon indicates that removing miR-HA-3p with antagomir-HA-3p can decrease the death rate of the H5N1 infected mice. This conclusion has also been confirmed in the experimental group treated with the H5N1 mutant strain. Compared with the mice injected with H5N1 (FIGS. 12A and 12C), the mice injected with the H5N1 mutant strain have a longer survival time (FIG. 12B) and slower weight loss rate (FIG. 12D). However, the mice injected with the mutant strain have obviously reduced survival rate (FIG. 12B) and faster weight loss rate (FIG. 12D) after being further injected with agomir-HA-3p, and as expected, the survival rate and body weight of the mice injected with the mutant strain and further injected with agomir have no significant change.

The results of this example indicate that the parasitic microorganism, highly contagious virus H5N1 IAV secretes a special kind of small ribonucleic acid, i.e., miR-HA-3p, and this ncRNA leads to the cytokine storm during the H5N1 infection by inhibiting the PCBP2 gene. The antagomir-HA-3p inhibitor is helpful in enhancing the resistance of mice to H5N1 and prolonging the survival time, so as to provide the basis for the development of H5N1 therapy.

(4) Application of Avian Influenza Virus or Avian Influenza miRNA

The miRNA of the present invention is used for: (a) the preparation of a reagent, a detecting chip or a kit for detecting avian influenza; (b) the preparation of a regulator for regulating the PCBP2 expression or activity; and (c) the preparation of reagents for regulating the expression of cytokines.

The nucleic acid chip for detecting avian influenza virus or avian influenza comprises: a solid-phase carrier; and oligonucleotide probes orderly immobilized on said solid-phase carrier, said oligonucleotide probe specifically capturing the miRNA of the present invention.

The nucleic acid chip for detecting avian influenza virus or avian influenza of the present invention can screen miRNA probes in a high-throughput way that stably change in serum, and furthermore predict and diagnose diseases through the overall change of miRNA in serum. We firstly determines that not less than one copy of miRNAs are present in serum by the sequencing or quantitative PCR method, then reverse complementary probes of these miRNAs are synthesized, and then these probes are spotted on a 75×25 mm chemically modified glass slide by a chip spotter SmartArray™. The samples spotted to the chip further include U6 as an interior label, tRNA, an artificially prepared external label with 30-base length, a positive control Hex, etc. The whole dot array is divided into four sub-arrays, each of which has 23 rows and 21 columns, with dot interval of 185 μm and dot diameter of about 130 μm, and each probe is replicated three times.

The chip operation process is as follows: (1) extraction of total RNA from serum/plasma, and detection of the mass of total RNA by formaldehyde denaturing gel electrophoresis; (2) isolation of miRNA: taking 50-100 μg of total RNA, and isolating miRNA with Ambion's miRNA Isolation Kit (Cat #. 1560); (3) fluorescence labelling of miRNA samples: performing fluorescence labelling with T4 RNA ligase labelling method, then precipitating with absolute ethyl alcohol, and blow-drying for chip hybridization; (4) hybridization and washing: dissolving the RNA in a 16 μL hybridization solution (15% formamide; 0.2% SDS; 3×SSC; and 50×Denhardt's solution), and hybridizing overnight at 42° C., and after hybridization, washing in a liquid containing 0.2% SDS and 2×SSC at about 42° C. for 4 minutes, then washing in 0.2×SSC at room temperature for 4 minutes, and drying the glass slide for scanning; (5) chip scanning: scanning the chip using a LuxScan 10K/A dual-channel laser scanner; and (6) data extraction and analysis: analyzing the chip image using a LuxScan 3.0 image analysis software, converting the image signals into digital signals, and finally choosing differentially expressed genes by SAM analysis.

The serum/plasma miRNA probes, e.g., miR-HA-3p, which have a large extent of differential expressions in avian influenza virus infections and under the normal physiological state by verification with both quantitative PCR technology and biochip technology can be used for the preparation of biochips, and the method is the same as above. Compared with traditional chips, this chip has no significant improvement on the manufacture process and operation procedure, but this chip simplifies the probe library, which will greatly reduce the production cost and production time of chip and can be easily prepared. It also increases the specificity and practicability of the chip. When this chip is put into practice, it can detect diseases at an early stage, which only needs the patient's serum/plasma without needing any other tissue, to help guide diagnosis and treatment.

In addition, the nucleic acid chip of the present invention is used to prepare a kit for detecting avian influenza virus or avian influenza. The kit for detecting avian influenza virus or avian influenza contains the nucleic acid chip of the present invention or the miRNA of the present invention.

The production process and operation procedure of the miRNA kit for the diagnosis and efficacy evaluation for avian influenza virus infections as well as the screening and efficacy evaluation of pharmaceutically active ingredients are based on quantitative and semi-quantitative PCR technology and biochip technology.

Firstly it is determined that not less than one copy of miRNAs are present in serum by the sequencing or quantitative PCR method. Then the serum/plasma miRNAs, e.g., miR-HA-3p, which have large expression and difference degree under a diseased state and under the normal physiological state are screened by quantitative PCR technology and biochip technology, as an indicator for predicting whether an avian influenza virus infection occurs and diagnosing the disease degree. Finally, the number of corresponding serum/plasma miRNAs is screened, and this is the optimized simplification made on the basis of the chip probe library. This kit comprises serum/plasma miRNA primers, Taq polymerase, dNTP and other reagents. The value of this kit is that it only needs serum/plasma without needing other tissue samples, and can detect the change trend of miRNA through the simplest probe library and then the likelihood of avian influenza infection occurrence can be predicted or the pathologic stages of avian influenza infections can be diagnosed according to this change trend. Therefore, this kit can be put into practice to increase the possibility of detecting avian influenza virus or avian influenza at an early stage to help guide diagnosis and treatment.

All the documents referred to in the present invention are incorporated by reference as if each reference cited as alone as a reference in the present application. In addition, it should be understood that after reading the teachings of the present invention described above, a skilled in the art can make various changes or modifications of the invention, and these equivalent forms also fall into the scope as defined by the appended claims of the present application.

The invention claimed is:

1. A pharmaceutical composition, wherein the pharmaceutical composition comprises a pharmaceutically acceptable carrier and an inhibitor for specifically inhibiting or blocking a RNA sequence, wherein the inhibitor is an antisense RNA sequence fully complementary to the RNA sequence which is selected from the group consisting of SEQ ID Nos.: 13, 14 and 15.

2. An inhibitor for specifically inhibiting or blocking RNA, wherein the inhibitor is an antisense RNA sequence fully complementary to a nucleotide sequence selected from the group consisting of SEQ ID Nos.: 13, 14 and 15.

3. The inhibitor of claim 2, wherein the inhibitor is the antisense RNA sequence which is completely complementary to the nucleotide sequence of SEQ ID No.: 14.

* * * * *

SEQUENCE LISTING

<160> NUMBER OF SEQ ID NOS: 16

<210> SEQ ID NO 1
<211> LENGTH: 24
<212> TYPE: RNA
<213> ORGANISM: Salmonella

<400> SEQUENCE: 1
ugugggcacu cgaagauacg gauu                                            24

<210> SEQ ID NO 2
<211> LENGTH: 27
<212> TYPE: RNA
<213> ORGANISM: Salmonella

<400> SEQUENCE: 2
augcgagagu agggaacugc caggcau                                         27

<210> SEQ ID NO 3
<211> LENGTH: 28
<212> TYPE: RNA
<213> ORGANISM: Salmonella

<400> SEQUENCE: 3
uccucuguag uucagucggu agaacggc                                        28

<210> SEQ ID NO 4
<211> LENGTH: 23
<212> TYPE: RNA
<213> ORGANISM: Salmonella

<400> SEQUENCE: 4
gaagguggcg gaauugguag acg                                             23

<210> SEQ ID NO 5
<211> LENGTH: 21
<212> TYPE: RNA
<213> ORGANISM: Salmonella

<400> SEQUENCE: 5
gcccggaugg uggaaucggu a                                               21

<210> SEQ ID NO 6
<211> LENGTH: 74
<212> TYPE: DNA
<213> ORGANISM: Artificial sequence
<220> FEATURE:
<223> OTHER INFORMATION: oligonucleotide

<400> SEQUENCE: 6
tgtgggcact cgaagatacg gattcttaac gtcctaggac gaaaaatgaa taccaagtct     60
caagagtgaa cacg                                                       74

<210> SEQ ID NO 7
<211> LENGTH: 24
<212> TYPE: RNA
<213> ORGANISM: Artificial sequence
<220> FEATURE:
<223> OTHER INFORMATION: oligonucleotide

<400> SEQUENCE: 7
aauccguauc uucgagugcc caca                                            24

-continued

```
<210> SEQ ID NO 8
<211> LENGTH: 27
<212> TYPE: RNA
<213> ORGANISM: Artificial sequence
<220> FEATURE:
<223> OTHER INFORMATION: oligonucleotide

<400> SEQUENCE: 8
augccuggca guucccuacu cucgcau                                          27

<210> SEQ ID NO 9
<211> LENGTH: 28
<212> TYPE: RNA
<213> ORGANISM: Artificial sequence
<220> FEATURE:
<223> OTHER INFORMATION: oligonucleotide

<400> SEQUENCE: 9
gccguucuac cgacugaacu acagagga                                         28

<210> SEQ ID NO 10
<211> LENGTH: 23
<212> TYPE: RNA
<213> ORGANISM: Artificial sequence
<220> FEATURE:
<223> OTHER INFORMATION: oligonucleotide

<400> SEQUENCE: 10
cgucuaccaa uuccgccacc uuc                                              23

<210> SEQ ID NO 11
<211> LENGTH: 21
<212> TYPE: RNA
<213> ORGANISM: Artificial sequence
<220> FEATURE:
<223> OTHER INFORMATION: oligonucleotide

<400> SEQUENCE: 11
uaccgauucc accauccggg c                                                21

<210> SEQ ID NO 12
<211> LENGTH: 20
<212> TYPE: DNA
<213> ORGANISM: Neisseria gonorrhoeae

<400> SEQUENCE: 12
gtatcccatc ctcgtcgcca                                                  20

<210> SEQ ID NO 13
<211> LENGTH: 22
<212> TYPE: RNA
<213> ORGANISM: Avian influenza virus H5N1

<400> SEQUENCE: 13
aggacuauuu ggagcuauag ca                                               22

<210> SEQ ID NO 14
<211> LENGTH: 22
<212> TYPE: RNA
<213> ORGANISM: Avian influenza virus H5N1

<400> SEQUENCE: 14
ggacuauuug gagcuauagc ag                                               22

<210> SEQ ID NO 15
```

```
<211> LENGTH: 22
<212> TYPE: RNA
<213> ORGANISM: Avian influenza virus H5N1

<400> SEQUENCE: 15
gaggacuauu uggagcuaua gc                                          22

<210> SEQ ID NO 16
<211> LENGTH: 20
<212> TYPE: RNA
<213> ORGANISM: Avian influenza virus H5N1

<400> SEQUENCE: 16
ggacuauuug gagcuauagc                                             20
```